US006809814B2

United States Patent
Xie et al.

(10) Patent No.: US 6,809,814 B2
(45) Date of Patent: Oct. 26, 2004

(54) SYSTEM AND METHOD FOR EPI-DETECTED COHERENT ANTI-STOKES RAMAN SCATTERING MICROSCOPY

(75) Inventors: Xiaoling Sunney Xie, Lexington, MA (US); Ji-Xin Cheng, Somerville, MA (US); Andreas Volkmer, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/345,677

(22) Filed: Jan. 16, 2003

(65) Prior Publication Data

US 2003/0160955 A1 Aug. 28, 2003

Related U.S. Application Data

(63) Continuation of application No. PCT/US01/19678, filed on Jun. 20, 2001.
(60) Provisional application No. 60/218,091, filed on Jul. 13, 2000.

(51) Int. Cl.$^7$ ............................. G01J 3/44; G01N 21/65
(52) U.S. Cl. ........................ 356/301; 356/317; 356/318
(58) Field of Search ................................. 356/301, 317, 356/318

(56) References Cited

U.S. PATENT DOCUMENTS

| | | |
|---|---|---|
| 4,284,354 A | 8/1981 | Liao |
| 4,405,237 A | 9/1983 | Manuccia et al. |
| 5,286,970 A | 2/1994 | Betzig et al. |
| 5,418,797 A | 5/1995 | Bashkansky et al. |
| 5,617,206 A | 4/1997 | Fay |
| 5,674,698 A | 10/1997 | Zarling et al. |
| 5,847,394 A | 12/1998 | Alfano et al. |
| 6,108,081 A | 8/2000 | Holtom et al. |
| 6,151,522 A | 11/2000 | Alfano et al. |
| 6,166,385 A | 12/2000 | Webb et al. |

FOREIGN PATENT DOCUMENTS

JP          03042553          2/1991

OTHER PUBLICATIONS

"Polarization– sensitive Coherent Anti–Stokes Raman Spectroscopy," Oudar et al. *Applied Physics Letters*. Jun. 1979. vol. 34 (11).
"Time–Dependent Fluorescence Depolarization Analysis in Three–Dimensional Microspectroscopy," Koshioka et al. *Applied Spectroscopy*. 1995. vol. 49, No. 2.
"Electromagnetic Theory of Propagation, Interference and Diffraction of Light," Born et al. *Principles of Optics*. Sixth Edition. 1989. p. 435–449.
"Polarization Cars Spectroscopy," Brakel et al. *Advances in Non–linear Spectroscopy*. 1988. John Wiley & Sons, Ltd.
"Coherent Ellipsometry of Raman Scattering of Light," Akhmanov et al. *JFTP Letters, American Institute of Physics*. 1977. vol. 25, No. 9.
"Optical Determination of Crystal Axis Orientation in Silicon Fragments or Devices," *IBM Technical Disclosure Bulletin*. Dec. 1984.

*Primary Examiner*—Frank G. Font
*Assistant Examiner*—Layla Lauchman
(74) *Attorney, Agent, or Firm*—Gauthier & Connors, LLP

(57) ABSTRACT

Systems and methods are disclosed for detecting a coherent anti-Stokes Raman scattering (CARS) signal from a microscopic sample in an epi-direction. In an embodiment, the system includes at least two sources having a pump source for generating a pump field at the pump frequency, a Stoke source for generating a Stoke field at the Stoke frequency that is different from the pump frequency, optics (64) for directing the pump and Stoke beams (60) in a collinear fashion through a focusing lens (66) toward a common focal spot in a sample (70), and detector optics that images the CARS in epi-direction, which is generated by the interaction of the pump and Stoke fields (60) with the sample (70) and is collected by the same focusing lens (66), towards an epi-detector (78).

16 Claims, 7 Drawing Sheets

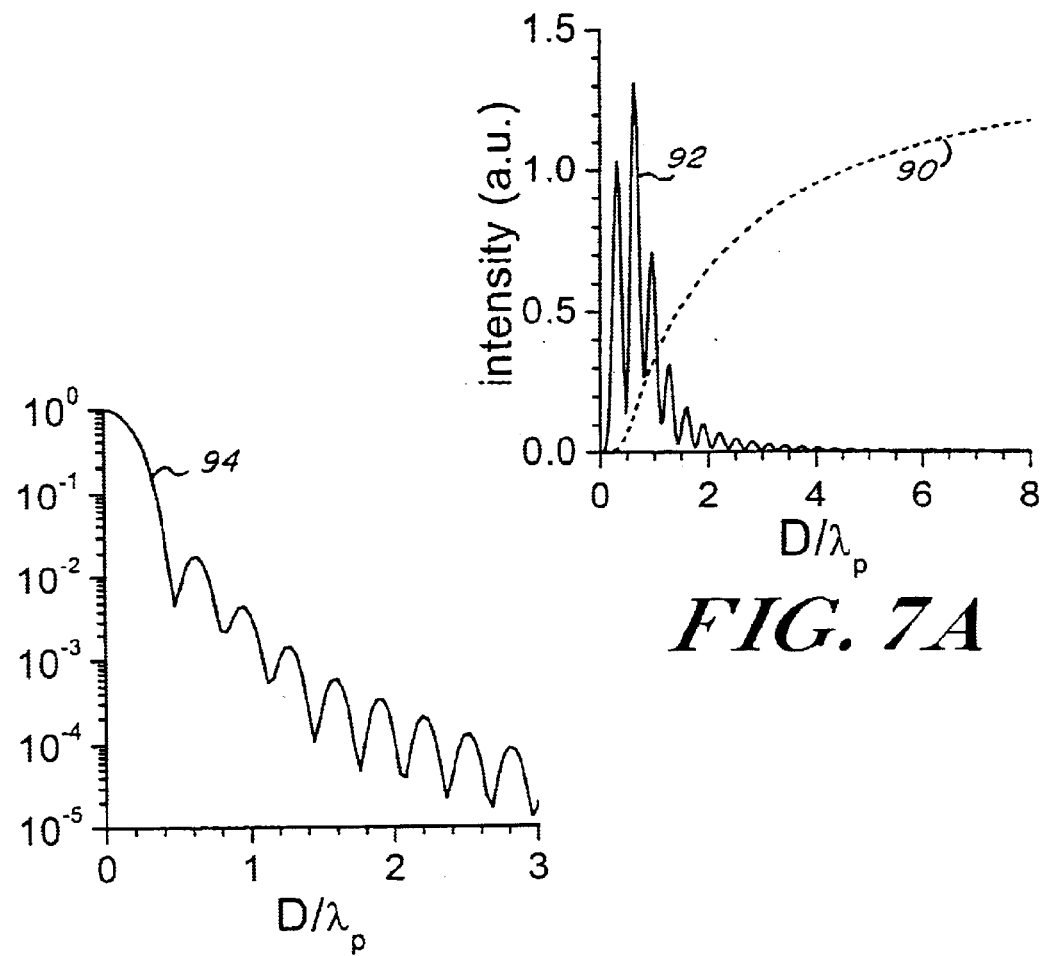
FIG. 7A
FIG. 7B
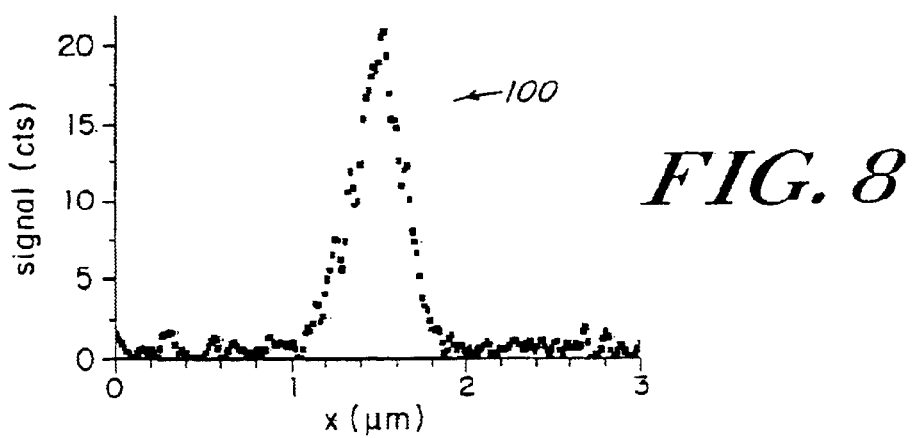
FIG. 8

SYSTEM AND METHOD FOR EPI-DETECTED COHERENT ANTI-STOKES RAMAN SCATTERING MICROSCOPY

This application is a continuation of PCT/US01/19678 filed Jun. 20, 2001 which claims the benefit of provisional application No. 60/218,091 filed Jul. 13, 2000.

BACKGROUND OF THE INVENTION

The invention relates to the field of microscopy, and particularly relates to the field of coherent anti-stokes Raman scattering microscopy.

Coherent anti-stokes Raman scattering (CARS) microscopy provides for the imaging of chemical and biological samples by using molecular vibrations as a contrast mechanism. In particular, CARS microscopy uses at least two laser fields, a pump electromagnetic field with a center frequency at $\omega_p$ and a Stokes electromagnetic field with a center frequency at $\omega_s$. The pump and Stokes fields interact with a sample and generate a coherent anti-Stokes field having a frequency of $\omega_{AS}=2\omega_p-\omega_s$ in the phase matched direction. When the Raman shift of $\omega_p-\omega_s$ is tuned to be resonant at a given vibrational mode, an enhanced CARS signal is observed at the anti-Stokes frequency $\omega_{AS}$.

Unlike fluorescence microscopy, CARS microscopy does not require the use of fluorophores (which may undergo photobleaching), since the imaging relies on vibrational contrast of biological and chemical materials. Further, the coherent nature of CARS microscopy offers significantly higher sensitivity than spontaneous Raman microscopy. This permits the use of lower average excitation powers (which is tolerable for biological samples). The fact that $\omega_{AS}>\omega_p, \omega_s$ allows the signal to be detected in the presence of background fluorescence.

For example, U.S. Pat. No. 4,405,237 discloses a coherent anti-Stokes Raman spectroscopic imaging device in which two laser pulse trains of different wavelengths, temporally and spatially overlapped, are used to simultaneously illuminate a sample. The signal beam in the phase matching direction with a two-dimensional detector, which gives the spatial resolution.

U.S. Pat. No. 6,108,081 discloses a different method and apparatus for microscopic vibrational imaging using coherent anti-Stokes Raman scattering. In the apparatus of the '081 patent, collinear pump and Stokes beams were focused by a high numerical aperture (NA) objective lens. The nonlinear dependence of the signal on the excitation intensity ensures a small probe volume of the foci, allowing three-dimensional sectioning across a thick sample. The signal beam is detected in the forward direction.

A prior art CARS imaging system (based on the '081 patent) 10 is shown diagrammatically in FIG. 1, in which collinear pump and Stokes beams 12 at frequencies of $\omega_p$ and $\omega_s$ respectively, are directed to a microscope objective lens 16, and onto a sample 18. The CARS signal is detected in the forward direction, and is received by collecting optics 20, filtered by one or more filters 22, and detected by a detector 26.

The signal beam that is created in CARS imaging, however, includes a substantial amount of background with no vibrational contrast from which the signal must be filtered or somehow distinguished. For example, as shown in FIG. 2, a conventional (forward-detected) lateral CARS intensity profile of a 535 nm polystyrene bead embedded in water includes a substantial amount of CARS background from water 30 in addition to the characteristic CARS signal from the bead 32. The horizontal axis in FIG. 2 represents the lateral dimension (in $\mu$m) across the scan area, and the vertical axis represents the strength of the CARS signal (in cts). The presence of this background from the isotropic bulk water has hindered efforts to increase the sensitivity of CARS imaging, particularly in biological applications. The CARS background is caused by a variety of circumstances. For example, because of electronic contributions to the third order nonlinear susceptibility, there exists a non-resonant contribution to the CARS signal of the sample of interest as well as of the surrounding isotropic bulk medium (i.e., solvent), which is independent of the Raman shift, surrounding isotropic bulk medium (i.e., solvent), which is independent of the Raman shift, $\omega_p-\omega_s$. In addition, in biological applications the common solvent water has strong resonant signals with broad spectral widths that may overwhelm the weak signal of the sample.

As shown in FIG. 3, a combined CARS image 40 and intensity profile 42 taken along line 44—44 of epithelial cells shows that the signal includes CARS background (as generally indicated at 46) that may not be easily distinguished from the microscopic sample signal (as generally indicated at 48). The lateral dimension (in $\mu$m) is shown along the horizontal axis, and signal strength (in cts) is shown along the vertical axis. In certain embodiments, these bulk solvent background contributions to the detected CARS signal may overwhelm the CARS sample signals.

There is a need, therefore, for a system and method for providing improved sensitivity of CARS microscopy, and in particular, to provide a CARS system that reduces the background from the bulk medium, and hence provides a higher signal-to-background ratio.

SUMMARY OF THE INVENTION

The invention provides systems and methods for detecting a coherent anti-Stokes Raman scattering signal from a microscopic sample. In one embodiment, the system includes at least two laser sources, a pump source for generating an electromagnetic field at the pump frequency, a Stokes source for generating an electromagnetic field at the Stokes frequency that is different from the pump frequency, optics to direct collinearly the pump and Stokes beams toward an objective lens, which provides a common focal spot, and a detector for measuring a coherent anti-Stokes signal in the backward (epi) direction that is generated by the interaction of pump and Stokes fields with the sample, and collected by the same lens focusing the pump and Stokes beams.

BRIEF DESCRIPTION OF THE DRAWINGS

The following detailed description of the illustrated embodiments may be further understood with reference to the accompanying drawings in which:

FIG. 7A shows a graphic illustration of calculated forward and epi-detected CARS signal intensities as a function of sphere diameter for tightly focused Gaussian excitation fields;

FIG. 7B shows a graphic illustration of the calculated ratio of epi-detected signal intensity to forward detected signal intensity as a function of sphere diameter for tightly focused Gaussian excitation fields;

FIG. 8 shows a graphic illustration of the lateral CARS intensity profile of a 535 nm polystyrene bead in water recorded in the epi-direction in accordance with an embodiment of the invention;

The drawings are for illustrative purposes only and are not to scale.

DETAILED DESCRIPTION OF THE ILLUSTRATED EMBODIMENTS

Figure 4A:
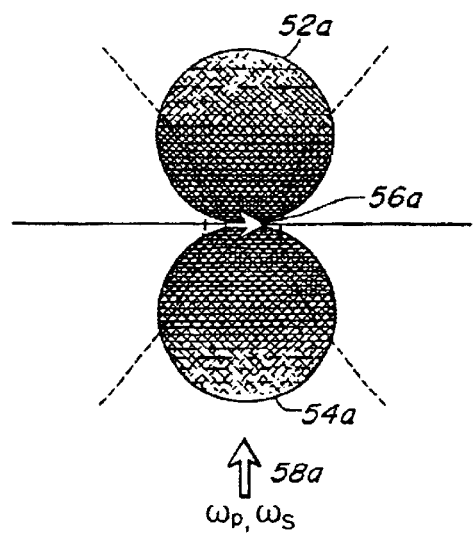
FIGS. 4A–4C show diagrammatic illustrations of the radiation pattern for a non-linear coherent CARS field for a sample comprising a single induced dipole, a mono-layer of induced dipoles, and an ensemble of induced dipoles of non-negligible thickness respectively.
Figure 4B:
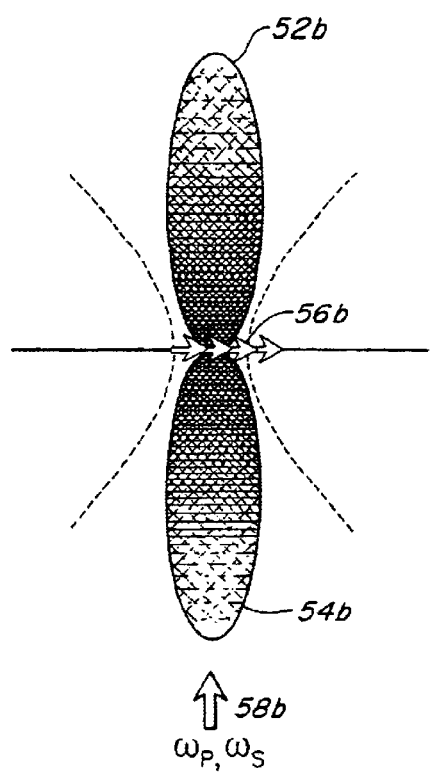
Figure 4C:
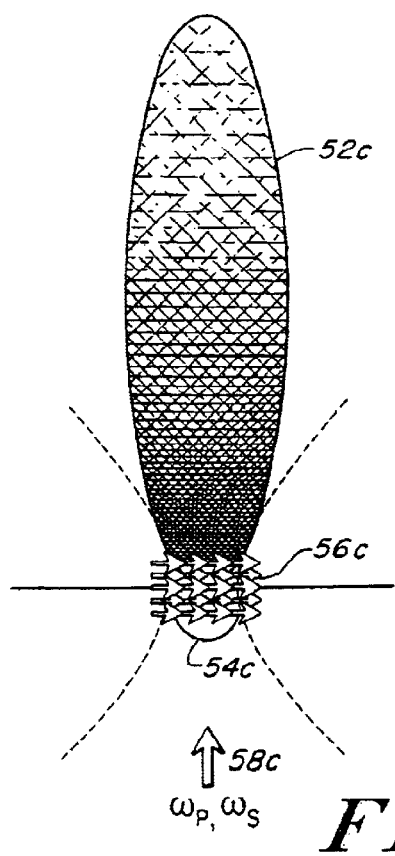

It has been discovered that when the size of the scatterer is smaller than the wavelength of the induced CARS field, for example cellular components in biological applications, then the radiation field of CARS emits in both the forward direction and in the backward direction with respect to the direction of incident pump and Stokes fields on the sample 56 as shown at 58 in FIG. 4. In the theoretical limit of a sample 56a having a single induced CARS dipole (see FIG. 4A), the backward directed portion 54a of the coherent radiation field equals the forward directed portion 52a, resembling the radiation field pattern of a Hertzian dipole. In a next example (see FIG. 4B) we consider a sample 56b comprising a monolayer of induced dipoles that extends perpendicularly to the direction of the incident pump and Stokes fields. The resulting radiation field pattern gains directionality along the propagation axis 58b of the incident fields, both in backward 54b and forward 52b directions with equal intensities. A sample 54c that resembles a bulk medium is conceptually realized by adding additional layers of induced dipoles in the vertical dimension. Constructive interference effects cause a built up of the coherent anti-Stokes field in the forward direction 52c, whereas deconstructive interference causes cancellation of any backward directed CARS radiation 54c (see FIG. 4C). This is the basis for the conventional phase matching condition in nonlinear coherent spectroscopy. The conventional phase matching condition breaks down when the sample size is smaller than the wavelengths. The coherent radiation of such sample is phase-matched in both forward and backward directions.

It is important to distinguish the coherent radiation in CARS from fluorescence. Emission in fluorescence microscopy is an incoherent summation of individual fluorophores. Therefore, the emission pattern is isotropic, and epi-detection (i.e., backward direction) is commonly used. Coherent summation in nonlinear coherent spectroscopy is fundamentally different. CARS has not been measured with epi-detection to date.

Signal detection in CARS microscopy has conventionally been performed in the forward direction with respect to the direction from which the pump and Stokes fields approach the sample. In contrast to conventional CARS signal detection, this invention involves the detection of CARS in the epi-direction 54. Based on the foregoing discussion, when the size of the sample is small, there is a CARS radiation field that is emitted in the backward direction, while the CARS background from the surrounding bulk medium is efficiently canceled in the epi-detection scheme. This results in high signal-to-background ratios and high sensitivity.

Figure 5:
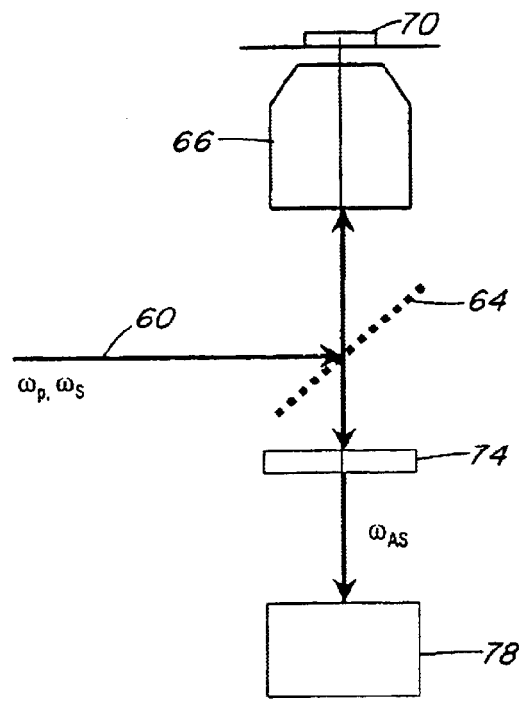
FIG. 5 shows a schematic illustration of an epi-detected CARS microscopy system in accordance with an embodiment of the invention.

As shown in FIG. 5, a system in accordance with an embodiment of the invention includes collimated and collinear pump and Stokes fields 60. The fields are generated by lasers at a pump frequency $(_p)$ and a Stokes frequency $(_s)$, and in further embodiments three fields may be used. Both fields 60 are directed to a high numerical aperture (NA) objective lens 66 by a dichroic beamsplitter 64, and lens 66 focuses both fields 60 to a common spot into the sample 70. The same lens 66 collects the backward (or epi) directed radiation field, which is then transmitted through the dichroic beamsplitter 64. The latter together with additional filters 74 spectrally isolates the CARS radiation before being detected. An epi-detected CARS signal is thereby received at the detector 78. In other embodiments, one or more lenses may be used to focus the epi-detected signal onto the detector 78. Conventional optical image scanning schemes (e.g. three-dimensional sample stage scanning or incident beam scanning) that are in communication with the detector 78 permit the sample to be thereby imaged.

Figure 6:
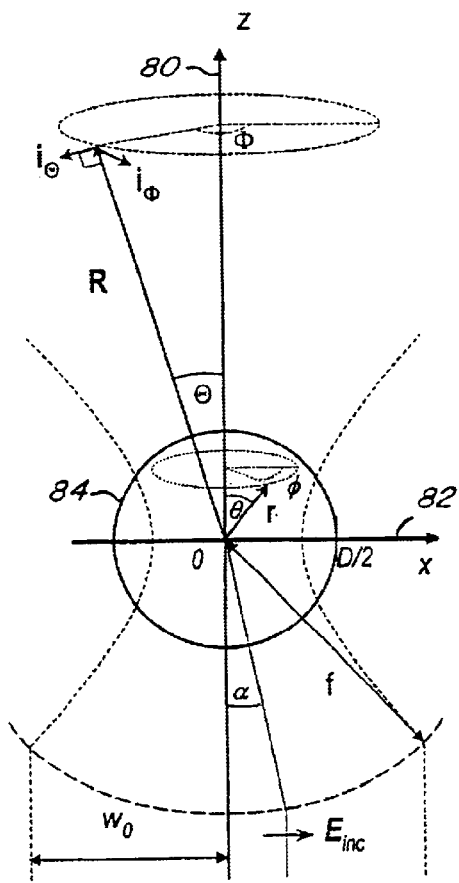
FIG. 6 shows a diagrammatic illustration of certain variables and relationships for analyzing CARS signals in theoretical simulations.

The underlying principle of the E-CARS microscope system of FIG. 5 may be qualitatively described by considering the physical picture in which the pump and Stokes fields are assumed to be monochromatic plane waves that propagate along the z axis as indicated at 80 in FIG. 6 through a slab sample having a thickness of D. The anti-Stokes field, $I_{AS}$, generated in the sample propagates in the forward direction (along z) and in the backward direction (along −z) with intensities defined as $$I_{AS}(D) = \frac{\pi}{2n_{AS}c} \omega_{AS}^2 D^2 |P^{(3)}|^2 sinc^2\left(\frac{|\Delta k|D}{2}\right)$$

where $P^{(3)}$ is the third-order polarization, c is the vacuum velocity of light, and $n_{AS}$ is the refractive index at the anti-Stokes angular frequency, $\omega_{AS}$. The phase mismatch is given by $\Delta k = k_{AS} - (2k_P - k_S)$, where $k_P$, $k_S$, and $k_{AS}$ represent the wave vectors of the pump, Stokes and anti-Stokes fields, which are defined as $|k_j| = 2\pi n_j/\lambda_j$ where j=P, S, AS, and $\lambda_j$ being vacuum wavelength. The phase matching condition is $|\Delta k|D << \pi$. For a very thin sample (D≈0), the phase matching condition is satisfied in both the forward direction ($k_{AS}$ along the z direction) and backward direction ($k_{AS}$ along the −z direction). This provides that the forward and backward CARS signals are equal in intensity for a thin sample. When D increases, however, the forward signal begins to overwhelm the backward signal because of the constructive interference in the forward direction and the destructive interference in the backward direction.

If the dispersion of the refractive index is negligible ($n = n_{AS} = n_P = n_S$), then the forward CARS signal ($|\Delta k| = 0$) has a quadratic dependence on D, $I_{AS}^F(D) \propto D^2$. Contribution to the signal from the solvent (large D) may, therefore, overwhelm the contribution from a thin sample (small D). In the case of epi-detected CARS ($|\Delta k|=4n\pi/\lambda_{AS}$), the signal oscillates as a function of D with a periodicity of $\lambda_{AS}/2n$, $I_{AS}^E(D) \propto \lambda_{AS}^2 \sin^2(2\pi n D/\lambda_{AS})$. The contribution from the solvent (large D) is significantly reduced as compared to that of the forward CARS signal. The fact that in the thin-sample-limit the forward- and backward-going CARS signals are equal, provides the basis for increasing the signal to background ratio for epi-detected CARS microscopy. The above analysis involved the assumption that the pump and Stokes signals are plane waves. Although these signals are actually tightly focused beams in the present embodiment, the physical picture described above remains the same.

With reference to FIG. 6, the forward and backward CARS signals for tightly focused beams may quantitatively analyzed by assuming that the incident pump and Stokes fields propagate along the optical axis z, and that they are linearly polarized along the x axis as indicated at 82. The incident fields are focused by a lens of focal length f having a numerical aperture N.A.=n sin $\alpha_{max}$, where $\alpha_{max}$ is the maximum cone angle $\alpha$ as shown in FIG. 6. The incident fields have Gaussian profiles with beam waists of $\omega_0$ before the lens, $E_j^{inc} = E_{j0} \exp(-f^2 \sin^2 \alpha/\omega_0^2)$, with j=P,S for the pump and Stokes fields respectively. Near the focal point, the field distribution is no longer Gaussian because of the breakdown of the paraxial approximation. The y and z components of the fields near the focal point are relatively small and can be neglected. The x component of the focal field in cylindrical coordinates is described as $$E_j(\rho, z) = \frac{1}{2} i k_j f e^{-i k_j f}$$
$$\int_0^{\alpha_{max}} E_j^{inc} \sqrt{\cos\alpha} (1+\cos\alpha) J_0(k_j \rho \sin\alpha) \sin\alpha e^{i k_j z \cos\alpha} d\alpha$$

where $\rho = \sqrt{x^2+y^2}$, and $J_0$ is the zero-order Bessel function.

A spherical sample 84 with a diameter D is placed at the origin of the overlapped foci of the pump and Stokes fields. Again assuming that any differences between the refractive indexes of the sample and solvent are negligible, the incident fields may be assumed to be unperturbed by the presence of the sample. Under the assumption of undepleted excitation, the incident fields induce a third-order polarization $P^{(3)}(r, \omega_{AS})$, of the sample at the anti-Stokes frequency, $\omega_{AS}$, as provided by:

$$P^{(3)}(r, \omega_{AS}) = \chi^{(3)}(\omega_{AS}) E_P^2(r) E_S^*(r)$$

where $\chi^{(3)}(\omega_{AS})$ is the third-order susceptibility, and $E_P(r)$ and $E_S(r)$ represent the focused pump and Stokes fields polarized along x.

The CARS radiation field per unit sample volume, $\vec{\epsilon}_{AS}(R, r, \omega_{AS})$, may be determined by calculating the Hertzian radiation field of the induced polarization, $P^{(3)}$, at $r=r(r,\theta,\phi)$. In the far-field, $|R|>>|r|$, the radiation field generated at r position assumes the following form, $$\vec{\epsilon}_{AS}(\Theta, \Phi, r)dV =$$
$$\frac{\omega_{AS}^2}{c^2} P^{(3)}(r, \omega_{AS}) \frac{e^{i(k_{AS}R - k_{AS}R \cdot r/R)}}{R} (\cos\Theta\cos\Phi i_\Theta - \sin\Phi i_\Phi) dV,$$

where $\Theta$ and $\Phi$ are the spherical coordinates specified by the vector $R(R,\Theta,\Phi)$. The unit vectors $i_\Theta$ and $i_\Phi$ denote transverse components orthogonal to R.

The CARS field is the coherent summation of the radiation field of induced polarization generated within the sample, which may be expressed as:

$$E_{AS}(\Theta,\Phi,D) = \int_0^{2\pi} d\phi \int_0^\pi d\theta \int_0^{D/2} dr \epsilon_{AS}(\Theta,\Phi,r) r^2 \sin\theta.$$

The radiation power from the scatterer ($P_{CARS}$), is calculated by integrating the Poynting vector over the angle ($\Theta_1 < \Theta < \Theta_2$) along the spherical surface of constant R as follows:

$$P_{CARS}(D) = \frac{cn}{8\pi} \int_{\Theta_1}^{\Theta_2} d\Theta \int_0^{2\pi} d\Phi |E_{AS}(\Theta, \Phi, D)|^2 R^2 \sin\Theta,$$

where the integration range $[\Theta_1, \Theta_2]$ is $[0, \alpha_{max}]$ for forward-detected CARS and $[\pi - \alpha_{max}, \pi]$ for epi-detected CARS, respectively.

As shown in FIG. 7A, the signal intensities (shown along the vertical axis) of the forward detected CARS signal 90 (×0.05) and the epi-detected CARS signal 92 diverge as the sphere diameter increases (shown in units of pump wavelengths along the horizontal axis). The forward detected CARS signal 90 increases quasi-quadratically with D and becomes saturated when D exceeds the longitudinal dimension of the focal excitation volume, i.e., full width at half maximum (FWHM)~1.2 $\mu$m for the experimental condition. The epi-detected CARS signal, however, appears only for small spheres and exhibits several maxima with the highest one at ~0.65 $_P$, and a periodicity close to that under the plane wave condition ($\lambda_{AS}/2n$). The epi-detected CARS signal intensity is negligible for spheres of large D, which resembles the case of focusing into an isotropic bulk medium. As shown in FIG. 7B, the ratio 94 of the intensities of the epi-detected CARS signal to the forward detected CARS signal establishes the presence of epi-detected CARS signals for small scatterers under the tightly focused condition. In the examples shown in FIGS. 7A and 7B, the pump and Stokes signal wavelengths were at $\lambda_P$=800 nm and $\lambda_S$=917 nm respectively. The numerical aperture of the lens was 1.4, and the index of refraction of the medium was 1.52.

In practice, the refractive index mismatch between the sample and the solvent, which is not considered in the calculation, can cause back-reflection of forward-going CARS (F-CARS). However, if the beams are not focused on an interface, the back-reflected F-CARS is defocused, and can be minimized by using confocal detection. If the size of the scatterer is small, the back-reflected F-CARS signal from the scatterer is negligible. For larger scatterers, however, the back-reflected CARS signal might be used as an additional contrast mechanism in epi-detection.

Figure 1:
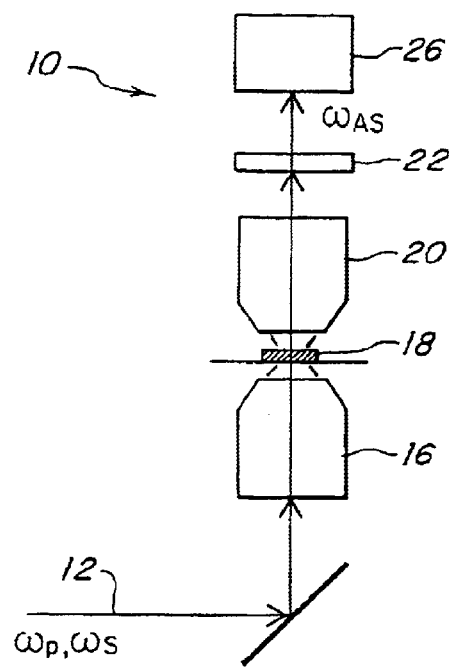
FIG. 1 shows a schematic illustration of a prior art CARS microscopy system.

In accordance with another embodiment of the invention, a CARS system that combined the elements of FIGS. 1 and 5 was developed for recording both the forward detected CARS signal and the epi-detected CARS signal simultaneously. A regeneratively amplified Ti:sapphire laser system that pumped an optical parametric amplifier (RegA 9000/OPA 9400, coherent) and operated at a repetition rate of 250 kHz was used to provide femtosecond pulses (FWHM 110 fs) for the excitation fields. Both linearly polarized pump and Stokes beams were temporally overlapped by an optical delay line, collinearly sent into an inverted optical microscope (Nikon TE 300 sold by Nikon Instruments, Inc. of Melville, N.Y.) and focused with an oil-immersion objective lens (Nikon Plan Apo, 60x, NA 1.4). The epi- and forward-detected CARS signals were spectrally filtered and confocally detected by avalanche photodiodes (SPCM-APD 200 sold by EG&G of Canada). CARS images were collected by raster scanning the sample with respect to the fixed laser beams using a closed-loop piezo-driven two-dimensional scanning stage. In other embodiments, the collinear pump and Stokes beams may be raster scanned with respect to the fixed sample.

Figure 2:
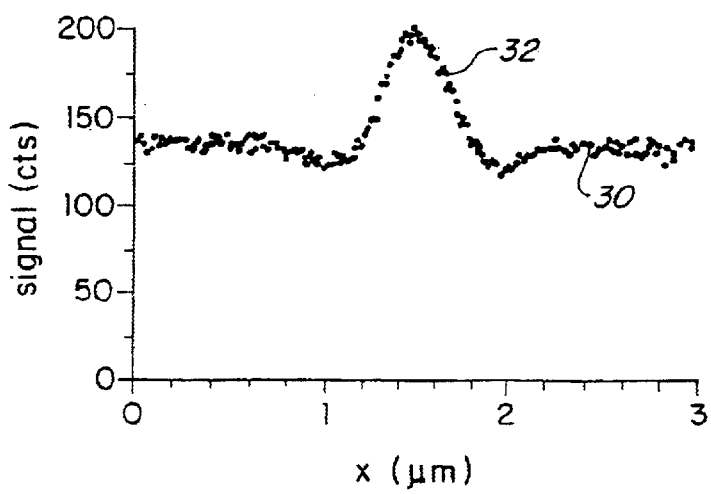
FIG. 2 shows a graphic illustration of a lateral CARS intensity profile of a 535 nm polystyrene bead in water recorded in accordance with the prior art CARS system shown in FIG. 1.

Polystyrene beads having a diameter of D=535±10 nm were spin coated on a glass cover slip and covered with water as test samples. The lateral profile of the forward detected CARS intensity is shown in FIG. 2, and the lateral profile of the simultaneously recorded epi-detected CARS signal is shown in 100 in FIG. 8. The CARS signals were confirmed by the quadratic and linear dependence on the incident pump and Stokes intensities, respectively. Because of the broad spectral bandwidth of the femtosecond excitation pulses (FWHM~300 cm$^{-1}$), the measured signal originates from several bands of polystyrene, i.e., the C—H bending (1447 cm$^{-1}$) and C=C stretching (1528 cm$^{-1}$ and 1602 cm$^{-1}$) vibrations. Imaging with a higher spectral resolution may also be achieved with a picosecond excitation pulses.

A comparison of FIGS. 2 and 8 illustrates the efficient rejection of isotropic bulk solvent contributions to the detected signal and the increase in sensitivity of the epi-detected CARS microscopy. The signal-to-background ratio for forward detected CARS was about 1.5, whereas that for epi-detected CARS was greater than 20. It has been found that the epi-detected CARS of pure water is more than a factor of 100 smaller than the simultaneously measured forward detected CARS, which is consistent with the illustration in FIG. 8.

Figure 9A:
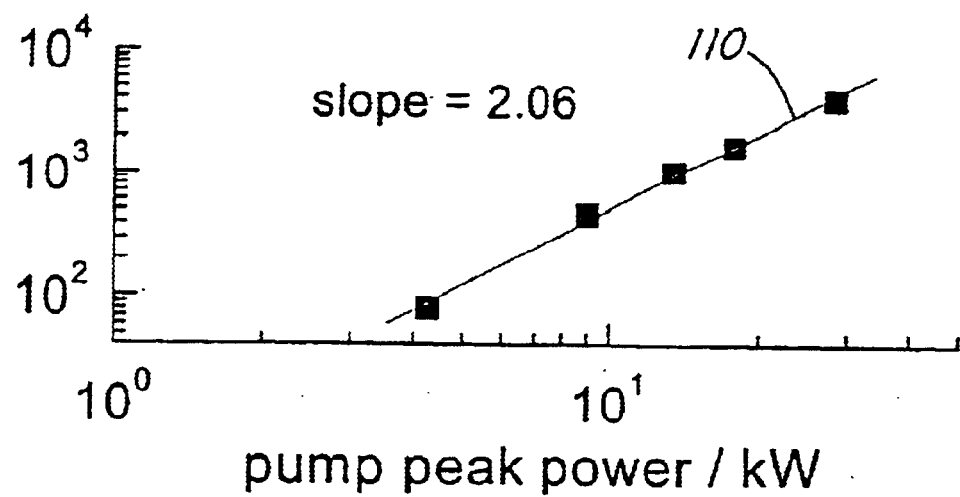
FIGS. 9A and 9B show graphic illustrations of epi-detected CARS intensity dependence on pump and Stokes power respectively for a 1 μm polystyrene bead.
Figure 9B:
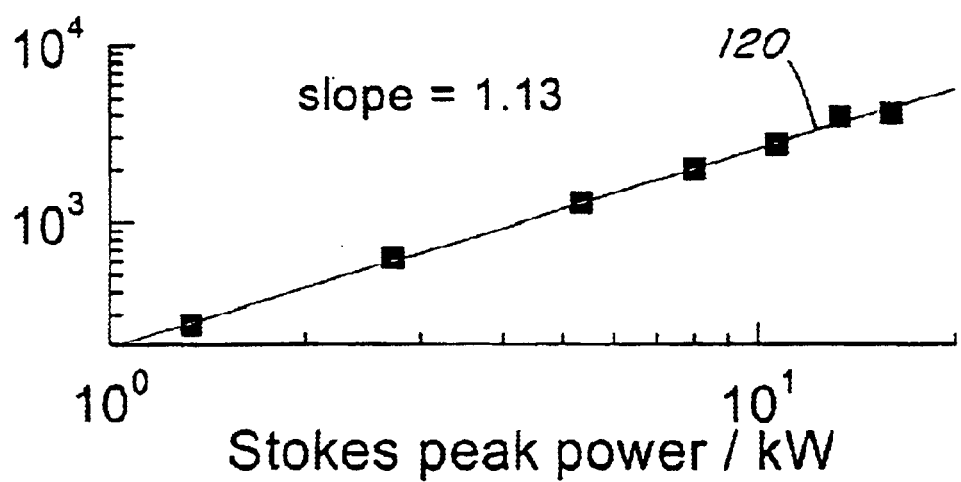

In accordance with another embodiment of the invention, a polystyrene bead having a diameter of 1 $\mu$m was imaged by an epi-detected CARS microscope system. Similar results to those discussed above were obtained. As shown in FIG. 9A at 110, the intensity of the epi-detected CARS signal exhibits a square-dependence on the pump peak power/kW, and as shown at 120 in FIG. 9B, the intensity of the epi-detected CARS signal is linearly dependent on the Stokes peak power/kW.

Figure 3:
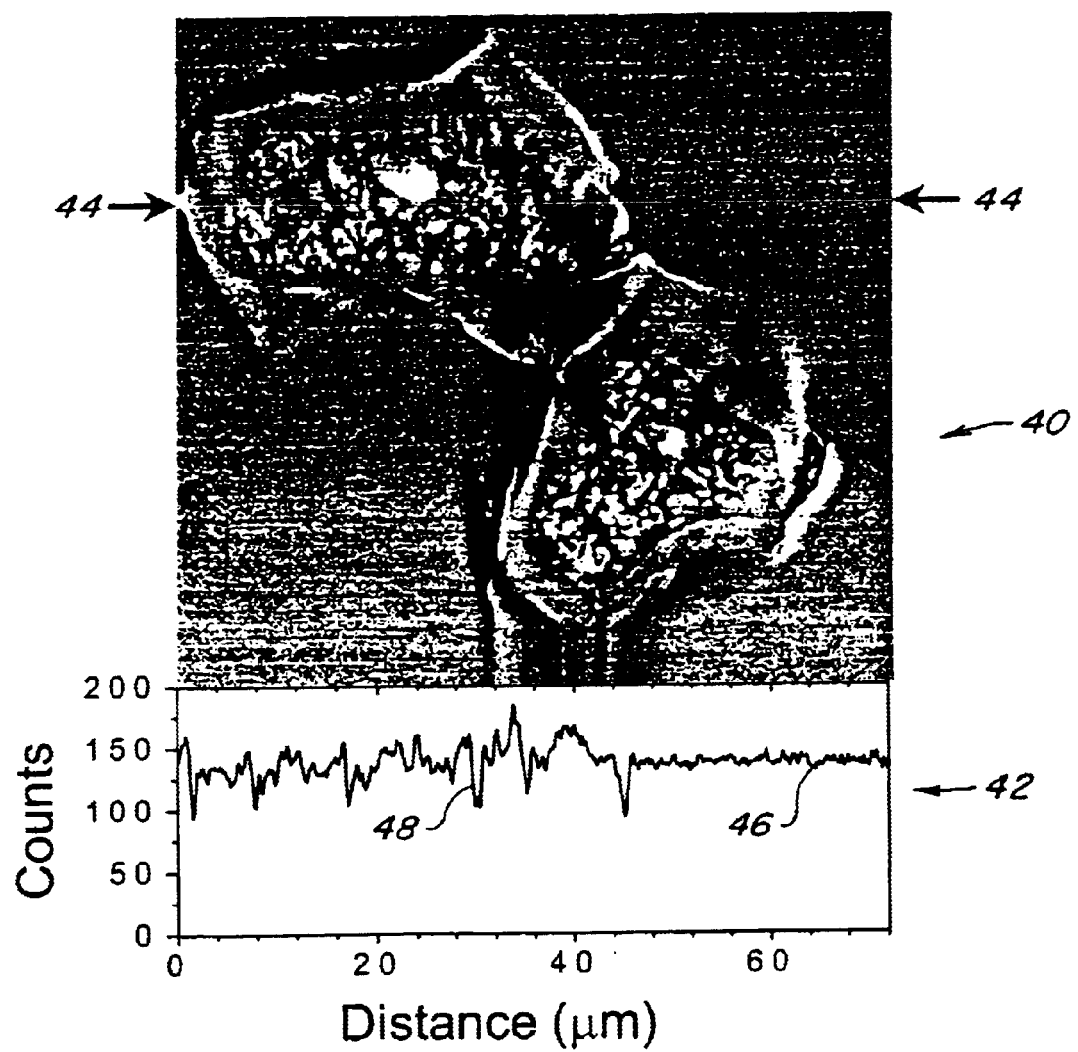
FIG. 3 shows a graphic illustration of a CARS image and lateral intensity profile of epithelial cells recorded in accordance with the prior art CARS system shown in FIG. 1.
Figure 10:
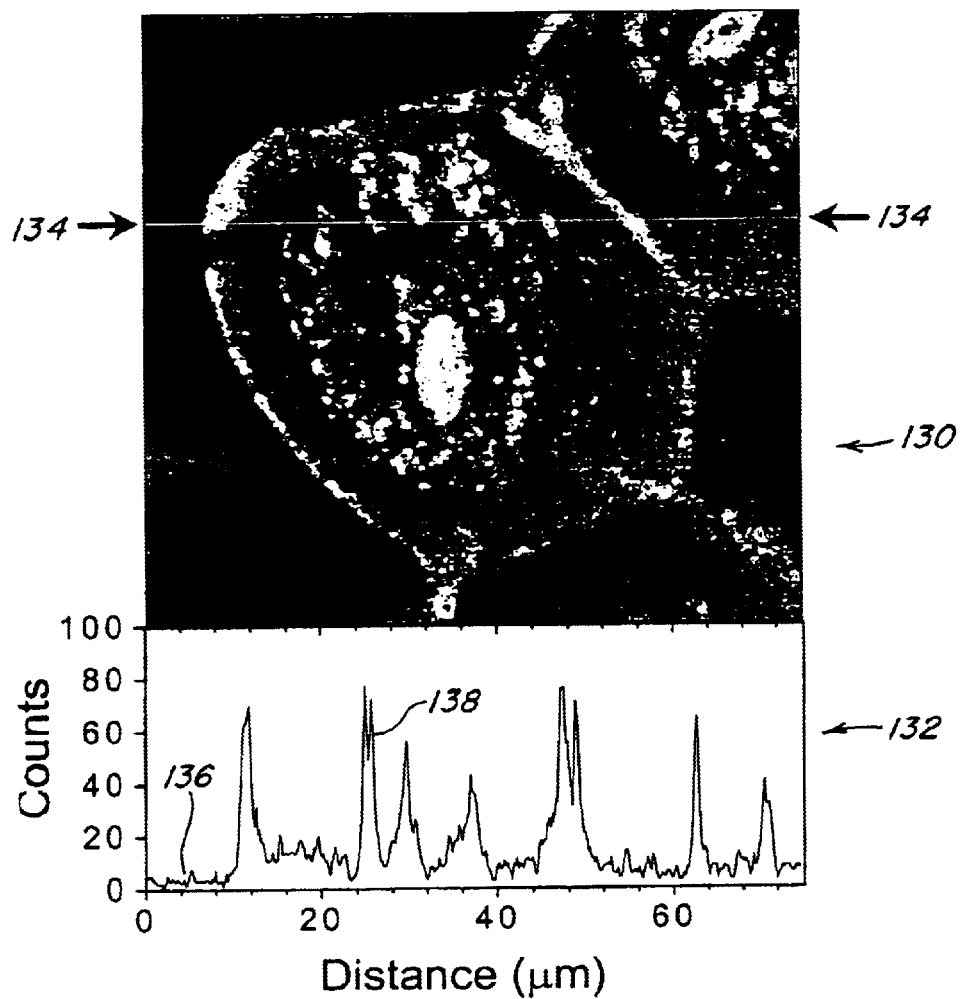
FIG. 10 shows a graphic illustration of an epi-detected CARS image and associated lateral intensity profile of epithelial cells in accordance with an embodiment of the invention.

In accordance with yet another embodiment of the invention, epi-detected CARS imaging of an unstained epithelial cell in an aqueous environment is illustrated in FIG. 10. The incident pump and Stokes fields were at 13333.2 cm$^{-1}$ and 11762.8 cm$^{-1}$ respectively, and the Raman shift was 1570 cm$^{-1}$, which is within the region of signature Raman bands of proteins and nucleic acids. The image size was about 512×512 (pixel)$^2$ with an integration time of 4.88 ms per pixel. The combined epi-detected CARS image 130 and lateral intensity profile 132 taken along line 134—134 illustrates the efficient rejection of the aqueous solvent signal (as generally indicated at 136), as well as the identification of small diffraction-limited features with high signal-to-background ratios (as generally indicated at 138). The nucleus, and other intracellular components are clearly observed with the epi-detection, which otherwise could not be seen with the forward-detected CARS as was the case with the image shown in FIG. 3. The image contrast disappears when the pump and Stokes pulses are not temporally or spatially overlapped.

The use of epi-detected CARS microscopy may significantly increase the sensitivity of CARS detection for scatterers that are smaller than the wavelength of light. This technique is particularly suited for intracellular imaging, although the invention may be employed in a wide variety of other applications where a small signal of a microscopic CARS scatterer has to be extracted from a relatively large CARS background originating from an isotropic bulk medium. It should be noted that the same concept of engineering the phase-matching condition by employing the epi-detection scheme is generally applicable to other nonlinear coherent microscopy schemes, such as but not limited to second harmonic generation, sum frequency generation and third harmonic generation. Epi-detected CARS may also be readily implemented with conventional confocal epi-fluorescence microscopes and provides improved sensitivity for point-by-point chemical mapping of living cells with vibrational spectroscopy.

Those skilled in the art will appreciate that numerous modifications and variations may be made to the above disclosed embodiments without departing from the spirit and scope of the invention.

What is claimed is:

1. A system for detecting a nonlinear coherent field induced in a microscopic sample, said system comprising:
    a first source for generating a first electromagnetic field at a first frequency;
    a second source for generating a second electromagnetic field at a second frequency that is different from said first frequency;
    optics for directing said first and second electromagnetic fields in a collinear fashion through a focusing lens toward a common focal volume in a first direction; and
    a detector for detecting a nonlinear coherent field that is generated in a second direction by the interaction of first and second electromagnetic fields in the focal volume, said second direction being substantially opposite to said first direction.

2. A system as claimed in claim 1, wherein said system further includes detector optics for directing the nonlinear coherent field that is generated in the second direction toward said detector.

3. A system as claimed in claim 2, wherein said system further includes a dichroic beamsplitter positioned between said focusing lens and said detector optics.

4. A system as claimed in claim 1, wherein said nonlinear coherent field is transmitted back through said focusing lens toward said detector.

5. A system as claimed in claim 1, wherein said system further includes a sample that is rasterscanned with respect to fixed beams.

6. A system as claimed in claim 1, wherein said system further includes beams that are rasterscanned with respect to a fixed sample.

7. A system for detecting a coherent anti-Stokes Raman scattering signal from a sample, said system comprising:
    a pump source for generating a pump field at a pump frequency;
    a Stokes source for generating a Stokes field at a Stokes frequency that is different from said pump frequency;
    optics for directing said pump and Stokes fields in a collinear fashion through a focusing lens toward a common focal volume in a forward direction; and
    an epi-direction detector for detecting a coherent anti-Stokes field that is generated from the focal volume in an epi-direction.

8. A system as claimed in claim 7, wherein said system further includes detector optics for directing the coherent anti-Stokes field toward said epi-direction detector.

9. A system as claimed in claim 7, wherein said system further includes a sample that is rasterscanned with respect to fixed beams.

10. A system as claimed in claim 7, wherein said system further includes beams that are rasterscanned with respect to a fixed sample.

11. A system as claimed in claim 7, wherein said coherent anti-Stokes field is transmitted back through said focusing lens and directed toward said epi-direction detector.

12. A system for detecting a coherent anti-Stokes Raman scattering signal from a sample, said system comprising:
    a pump source for generating a pump field at a pump frequency;

a Stokes source for generating a Stokes field at a Stokes frequency that is different from said pump frequency;

optics for directing said pump and Stokes fields in a collinear fashion through a focusing lens toward a common focal volume in a forward direction;

a forward direction detector for detecting a coherent anti-Stokes field that is generated from the focal volume in a forward direction; and an epi-direction detector for detecting a coherent anti-Stokes field that is generated from the focal volume in an epi-direction.

13. A method of detecting a nonlinear coherent field induced in a microscopic sample, said method comprising the steps of:

generating a first electromagnetic field at a first frequency;

generating a second electromagnetic field at a second frequency that is different from said first frequency;

directing said first and second electromagnetic fields in a collinear fashion through a focusing lens toward a common focal volume in a first direction; and detecting a nonlinear coherent field that is generated in a second direction by the interaction of the first and second electromagnetic fields in the focal volume, said second direction being substantially opposite to said first direction.

14. A method as claimed in claim 13, wherein said method further includes the step of directing the nonlinear coherent field from the focal volume back through said focusing lens.

15. A method of detecting a coherent anti-Stokes Raman scattering signal from a sample, said method comprising the steps of:

generating a pump field at a pump frequency;

generating a Stokes field at a Stokes frequency that is different from said pump frequency;

directing said pump and Stokes fields in a collinear fashion through a focusing lens toward a common focal volume [element] in a forward direction; and detecting a coherent and-Stokes field that is generated from the sample volume in an epi-direction.

16. A system for detecting a nonlinear coherent field induced in a microscopic sample, said system comprising:

a first source for generating a first electromagnetic field at a first frequency;

a second source for generating a second electromagnetic field at a second frequency that is different from said first frequency;

optics for directing said first and second electromagnetic fields through a focusing lens toward a common focal volume; and a detector for detecting a nonlinear coherent field from the focal volume back through the focusing lens by the interaction of first and second electromagnetic fields in the focal volume.

* * * * *

UNITED STATES PATENT AND TRADEMARK OFFICE
CERTIFICATE OF CORRECTION

PATENT NO. : 6,809,814 B2
DATED : October 26, 2004
INVENTOR(S) : Xiaoling Sunney Xie et al.

It is certified that error appears in the above-identified patent and that said Letters Patent is hereby corrected as shown below:

Column 10,
Line 10, remove "[element]"
Line 11, remove "and" and replace with -- anti --

Signed and Sealed this

First Day of February, 2005

JON W. DUDAS
*Director of the United States Patent and Trademark Office*